US006329571B1

(12) United States Patent
Hiei

(10) Patent No.: US 6,329,571 B1
(45) Date of Patent: Dec. 11, 2001

(54) METHOD FOR TRANSFORMING INDICA RICE

(75) Inventor: Yukoh Hiei, Shizuoka (JP)

(73) Assignee: Japan Tobacco, Inc., Tokyo (JP)

( * ) Notice: Subject to any disclaimer, the term of this patent is extended or adjusted under 35 U.S.C. 154(b) by 0 days.

(21) Appl. No.: 09/091,666

(22) PCT Filed: Oct. 22, 1997

(86) PCT No.: PCT/JP97/03806

§ 371 Date: Aug. 24, 1998

§ 102(e) Date: Aug. 24, 1998

(87) PCT Pub. No.: WO98/17813

PCT Pub. Date: Apr. 30, 1998

(30) Foreign Application Priority Data

Oct. 22, 1996 (JP) .................................................... 8-298039

(51) Int. Cl.$^7$ .............................. A01H 1/00; C12N 15/82; C12N 15/87
(52) U.S. Cl. ......................... 800/294; 800/278; 800/268; 800/320.2
(58) Field of Search ................................ 800/320, 320.2, 800/278, 268, 294; 536/24.1; 435/469

(56) References Cited

U.S. PATENT DOCUMENTS 5,591,616    1/1997    Hiei et al. .

FOREIGN PATENT DOCUMENTS

| 0504869A2 | 9/1992 | (EP) . |
| 0672752A1 | 9/1995 | (EP) . |
| 4-222527  | 8/1992 | (JP) . |
| 4222527A  | 8/1992 | (JP) . |

OTHER PUBLICATIONS

Rance et. al. Partial Desiccation of Mature embryo–derived calli . . . Plant Cell Reports (1994) 13:647–651.*
Li et. al. An improved rice transformation system using the biolistic method. Plant Cell Reports (1993) 12:250–255.*
Hiei et al. Efficient Transformation of rice mediated by Agrobacterium . . . The Plant Journal (1994)6(2), 271–282.*
Evans et. al. Plant Cell culture media. Handbook of Plant Cell Culture, vol. 1, p. 61, 1983.*
Bao–Jian et al., *Science in China (Series B)*, vol. 34, No. 1, pp. 54–64 (Jan. 1991).
Vijayachandra et al., *Plant Molecular Biology*, vol. 29, pp. 125–133 (1995).
Rasnid et al., *Plant Cell Reports*, vol. 15, pp. 727–730 (1996).
Aldemita et al., *Planta*, vol. 199, pp. 612–617 (1996).
Rance et al., *Plant Cell Reports*, vol. 13, pp. 647–651 (1994).
Hiei et al., *The Plant Journal*, vol. 6, No. 2, pp. 271–282 (1994)..

Potrykus, *Bio/Technology*, pp. 535–542 (Jun. 1990).
Li et al., *Plant Cell Reports*, vol. 12, pp. 250–255 (1993).
Chan et al., *Plant Cell Physiol.*, vol. 33, No. 5, pp. 577–583 (1992).
Christou et al., *Tibtech*, vol. 10, pp. 239–246 (Jul. 1992).
Glaszmann, *Theor Appl Genet*, vol. 74, pp. 21–30 (1987).
Hood et al., *Bio/Technology*, pp. 702–709 (Aug. 1984).
Hood et al., *Journal of Bacteriology*, vol. 168, No. 3, pp. 1283–1290 (Dec. 1986).
Komari et al., *Journal of Bacteriology*, vol. 166, No. 1, pp. 88–94 (Apr. 1986).
Jin et al., *Journal of Bacteriology*, vol. 169, No. 10, pp. 4417–4425 (Oct. 1987).
Komari, *Plant Science*, vol. 60, pp. 223–229 (1989).
Horsch et al., Abstract, *Science*, vol. 223, pp. 496–498 (Feb. 1984).
Herrera–Estrella et al., *The EMBO Journal*, vol. 2, No. 6, pp. 987–995 (1983).
Ditta et al., *Proc. Natl. Acad. Sci. USA*, vol. 77, No. 12, pp. 7347–7351 (Dec. 1980).
Chilton et al., *Proc. Nat. Acad. Sci. USA*, vol. 71, No. 9, pp. 3672–3676 (Sep. 1974).
Bao–Jian et al., *Science in China* (Series B), vol. 34, No. 1, pp. 54–64 (Jan. 1991).
Vijayachandra et al., *Plant Molecular Biology*, vol. 29, pp. 125–133 (1995).
Rashid et al., *Plant Cell Reports*, vol. 15, pp. 727–730 (1996).
Aldemita et al., *Planta*, vol. 199, pp. 612–617 (1996).
Christou et al., *Bio/Technology*, vol. 9, pp. 957–963 (Oct. 1991).
Rance et al., *Plant Cell Reports*, vol. 13, pp. 647–651 (1994).
Hiei et al., *The Plant Journal*, vol. 6, No. 2pp. 271–282 (1994).
Potrykus, *Bio/Technology*, pp. 535–542 (Jun. 1990).
Li et al., *Plant Cell Reports*, vol. 12, pp. 250–255 (1993).
Chan et al., *Plant Cell Physiol.*, vol. 74, pp. 21–30 (1987).
Christou et al., *Tibtech*, vol. 10, pp. 239–246 (Jul. 1992).
Glaszmann, *Theor Appl Genet*, vol. 74, pp. 21–30 (1987).
Hood et al., *Bio/Technology*, pp. 702–709 (Aug. 1984).
Hood et al., *Journal of Bacteriology*,

* cited by examiner

*Primary Examiner*—Gary Benzion
(74) *Attorney, Agent, or Firm*—Birch, Stewart, Kolasch & Birch, LLP

(57) ABSTRACT

A method for transforming Indica rice with a high efficiency is disclosed. In the method of the present invention, immature embryo cells of Indica rice are transformed by Agrobacterium method, and the transformed cells are selected. As the medium for selecting the transformed cells, a medium containing 2000 to 4000 mg/l of $KNO_3$, 60 to 200 mg/l of $MgSO_4$, 200 to 600 mg/l of $KH_2PO_4$, 100 to 450 mg/l of $CaCl_2$, 200 to 600 mg/l of $(NH_4)_2.SO_4$, 1 to 7 mg/l of $H_3BO_3$, 2 to 20 mg/l of $MnSO_4$, 20 to 50 mg/l of EDTA or a salt thereof, 3 to 8 mg/l of Fe, 50 to 200 mg/l of myoinositol, 0.5 to 10 mg/l of 2,4-dichlorophenoxyacetic acid, 0.01 to 5 mg/l of a cytokinin, 5000 to 80,000 mg/l of a sugar, and a gelling agent, which medium has a pH of 4.5 to 6.5, is used.

10 Claims, 1 Drawing Sheet

METHOD FOR TRANSFORMING INDICA RICE

This application is the national phase under 35 U.S.C. §371 of prior PCT International Application No., PCT/JP97/03806, which has an International filing date of Oct. 22, 1997, which designated the United States of America, the entire contents of which are hereby incorporated by reference.

TECHNICAL FIELD

The present invention relates to method for transforming rice by the Agrobacterium method.

BACKGROUND ART

Conventional methods for transforming rice include electroporation method and PEG method using protoplasts, and these methods have been applied to Japonica rice which may easily be cultured. However, these methods may be applied only to the varieties for which redifferentiation system from protoplasts have been established, and have scarcely been applied to Indica rice which is difficult to culture.

Since the particle gun method does not need a protoplast-culturing system and so it can be applied to various varieties, the method has been more and more used in a number of laboratories. In general, it is thought that Indica rice varieties, especially those belonging to the so called Group I (Glaszmann J. C. (1987) Isozymes and classification of Asian rice varieties. Theor. Appl. Genet. 74:21–30) which occupies most part of the Indica rice varieties, are difficult to culture. However, the transformation efficiency of the varieties belonging to Group I by the particle gun method reported by Christou et.al. (Christou P., Ford, T. L. and Kofron, M. (1992) The development of a variety-independent gene-transfer method for rice. TIB TECH 10: 239–246), is as low as 2 to 3% per immature embryo. According to the recent report by other groups too, a transformation system with a high efficiency has not been obtained (LiL., Rongda, Q., Kochko, A., Fauquet, C. and Beachy, R. N. (1993), An improved rice transformation system using the biolistic method. Plant Cell Report 12: 250–255).

On the other hand, the Agrobacterium method has been widely used for dicotyledons as a simple and stable transformation method. However, it was thought that the Agrobacterium method could not be applied to monocotyledons such as rice (Potrykus I., (1990) Gene transfer to cereals: an assessment Bio/technology 8:535–542). Recently, it has been proved that the Agrobacterium method may be applied to rice which is a monocotyledon (WO94/00977; WO95/06722; Hiei Y., Ohta, S., Komari, T. and Kumashiro, T. (1994) Efficient transformation of rice (Oryza Sativa L.) mediated by transformation by Agrobacterium and sequence analysis of the boundaries of the T-DNA. The Plant Journal 6:271–282), so that future development of this method as a useful transformation method is expected.

On the other hand, Rance et al. disclose an NB medium useful for inducing a callus having redifferentiation ability from mature seeds of Indica rice (Iann M. Rance,I. M. et al., Partial desiccation of mature embryo-derived calli, a simple treatment that dramatically enhances the regeneration ability of Indica rice, Plant Cell Reports (1994) 13:647–651). However, they did not investigate the effect of the NB medium on the selection of the transformed cells. Li et al. reported transformation of Japonica rice with high efficiency using a medium similar to NB medium (not containing NAA, BA and L-glutamine) (Li L. et al., (1993) An improved rice transformation system using the biolistic method. Plant Cell Report 12: 250–255). However, they reported that transformants of Indica rice were not obtained with a high efficiency. Further, Li et al. did not study application of the medium to the Agrobacterium method.

As mentioned above, the methods in which transformants are prepared from protoplasts have a problem that they cannot be applied to the varieties for which a regeneration system from protoplasts has not been established. As for the particle gun method, the transformation efficiencies of the reported methods for the varieties which are difficult to culture, such as the varieties belonging to Indica rice, are low.

Thus, it is thought that the Agrobacterium method may be a candidate for the method for transforming Indica rice. As mentioned above, transformation of Japonica rice by the Agrobacterium method is known. The present inventors investigated whether the method applied to Japonica rice may be applied to Indica rice or not.

The first candidate for the method for transforming rice by Agrobacterium is the method using a dedifferentiated tissue as described in WO94/00977 and Hiei et al. (1994). Thus, the present inventors tried to introduce gene by Agrobacterium into a callus, using several varieties of Indica rice belonging to Group I. As a result, it was proved that transformants could be obtained although the number was small. However, a transformation system having reproducibility could not be established. In cases where transformation is performed on a callus, it is necessary to employ a callus having a high cell-dividing ability and high regeneration ability. However, for rice varieties which are difficult to culture, it is not easy to induce a callus having high cell-dividing activity, which is suited for introduction of a gene. Therefore, it is thought that in cases where a callus is used as the sample tissue, the varieties to which this method can be applied is limited, and transformants cannot be obtained easily for the varieties which are difficult to culture.

As a method employing a tissue other than callus, it is thought that the method employing an immature embryo may be applied. However, if the method described in WO95/06722 or EP-A-0 672 752, which is effective for Japonica rice, is applied to Indica rice as it is, the transformation efficiency was low, so that a practical transformation system could not be established.

DISCLOSURE OF THE INVENTION

Accordingly, an object of the present invention is to provide a method by which Indica rice can be transformed with a high efficiency.

The present inventors intensively studied to discover that high transformation efficiency may be attained for Indica rice by using a medium based on the above-described NB medium by Rance et al., as the medium used in the selection step of the transformed cells in the method described in WO95/06722 and EP-A-0672752 in which immature embryo cells of rice are transformed by Agrobacterium, thereby completing the present invention.

That is, the present invention provides a method for transforming rice comprising transforming immature embryo cells of Indica rice by Agrobacterium method and selecting transformed cells, characterized in that a medium containing 2000 to 4000 mg/l of $KNO_3$, 60 to 200 mg/l of $MgSO_4$, 200 to 600 mg/l of $KH_2PO_4$, 100 to 450 mg/l of $CaCl_2$, 200 to 600 mg/l of $(NH_4)_2.SO_4$, 1 to 7 mg/l of $H_3BO_3$, 2 to 20 mg/l of $MnSO_4$, 20 to 50 mg/l of EDTA or a salt thereof, 3 to 8 mg/l of Fe, 50 to 200 mg/l of myoinositol, 0.5 to 10 mg/l of 2,4-dichlorophenoxyacetic acid, 0.01 to 5 mg/l of a cytokinin, 5000 to 80,000 mg/l of a sugar, and a gelling agent, which medium has a pH of 4.5 to 6.5, is used as a medium for selecting the transformed cells.

By the present invention, it was first attained to transform Indica rice with a high efficiency, of which transformation efficiency was hitherto low and which cannot be transformed reproducibly.

BEST MODE FOR CARRYINT OUT THE INVENTION

Figure 1:
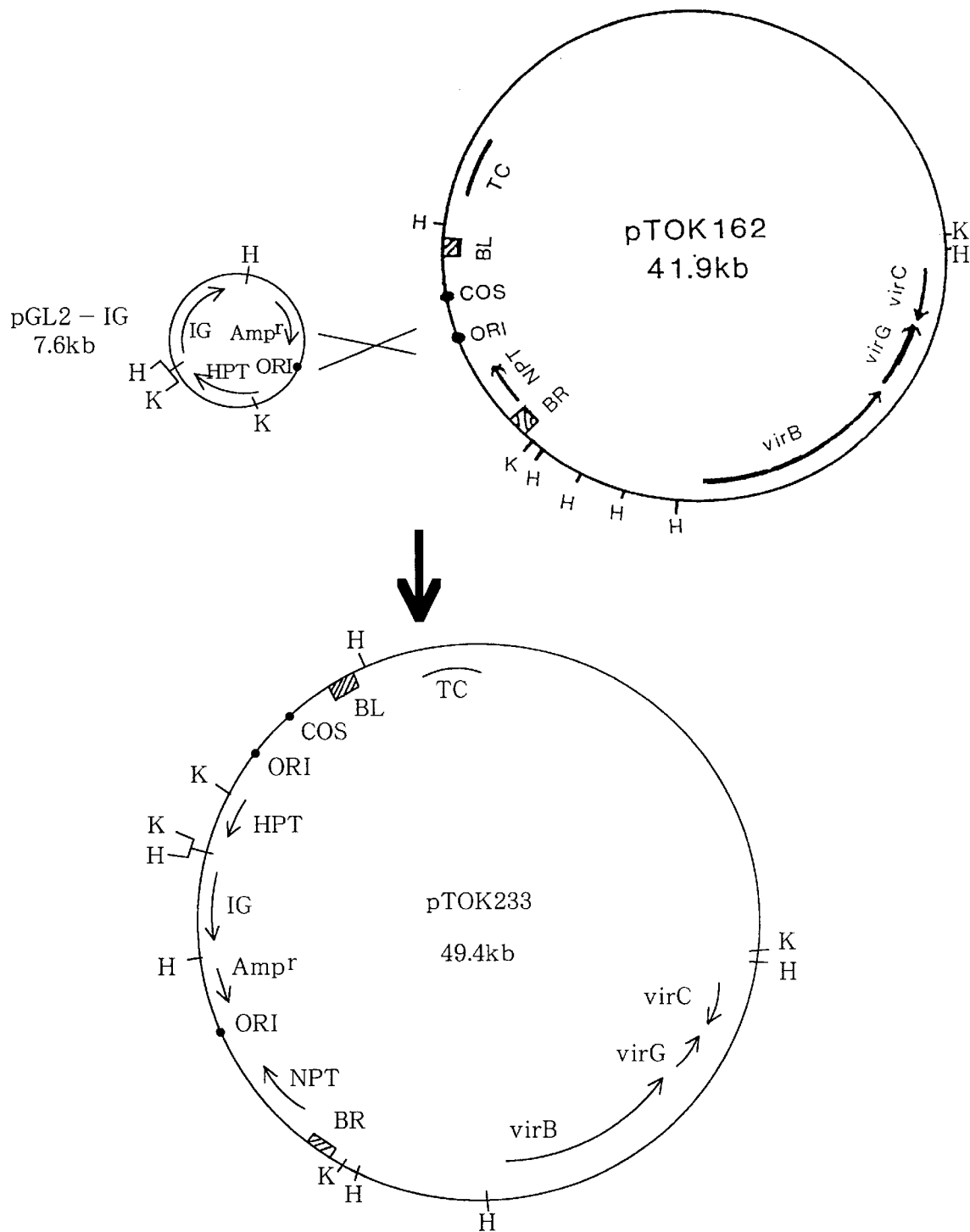
FIG. 1 shows the structures of super binary vectors pTOK162 and pTOK233 which may preferably be used in the method of the present invention.

The cells subjected to the transformation method according the present invention are immature embryo cells of Indica rice. The Indica rice is not restricted. However, the present invention is especially useful when applied to those belonging to Group I (Glaszmann, supra) which are difficult to transform by the conventional methods. Examples of the varieties belonging to Group I of Indica rice include IR8, IR24, IR26, IR36, IR54, IR64 IR72, Xin Qing Ai, Nan Jin 11, Suewon 258 and the like, but the varieties belonging to Group I of Indica rice are not restricted to these.

The term "immature embryo" herein means the embryo of an immature seed which is in the stage of maturing after pollination. The maturing stage of the immature embryos to be treated by the method of the present invention are not restricted and the collected embryos may be in any stage after pollination. Preferred embryos are those collected on not less than 2 days after their fertilization. The immature embryos may preferably be inbreds, F1 between inbreds, F1 between an inbred and a naturally-pollinated variety, and commercial F1 varieties. Among the embryos, scutellum cells are preferred. It is not necessary to subject the immature embryos to a dedifferentiation treatment before contacting the immature embryos with Agrobacterium. "Dedifferentiation treatment" herein means a process of obtaining cell clusters, such as callus, that show unorganized growth by culturing differentiated cells of plant tissues on a dedifferentiation medium.

As the Agrobacterium to be used for the transformation, Agrobacterium which have Ti plasmid or Ri plasmid and which have heretofore been employed for the transformation of dicotyledons can be employed. Many of these Agrobacterium contain a vector having a DNA region originated from the virulence region (vir region) of Ti plasmid originated from *Agrobacterium tumefaciens*. The gene encoding the character which is desired to be given to the plant is inserted in this vector, or exists in a separate plasmid and inserted into the Ti plasmid in vivo by homologous recombination or the like. Komari et al. developed a vector containing a DNA region originated from the virulence region (vir region) of Ti plasmid pTiBo542 contained in a highly virulent *Agrobacterium tumefaciens* A281 having an extremely high transformation efficiency (Hood, E. E. et al., 1984; Biotech. 2:702–709, Hood, E. E. et al., 1986; J. Bacteriol. 168:1283–1290, Komari, T. et al., 1986; J. Bacteriol. 166:88–94, Jin, S. et al., 1987; J. Bacteriol. 169:4417–4425, Komari, T., 1989; Plant Science, 60:223–229, ATCC 37349) (Japanese Laid-Open Patent Application (Kokai) No. 4-222527). In this specification, the vector having the virulence region of Ti plasmid pTiBo542 contained in *Agrobacterium tumefaciens* A281, left and right border sequences of T-DNA of a Ti plasmid or an Ri plasmid of a bacterium belonging to the genus Agrobacterium, and a desired gene located between said left and right border sequences is called a "super binary vector". In the present invention, such a super binary vector may preferably be used.

An example of such a super binary vector is pTOK162 (Japanese Laid-Open Patent Application (Kokai) No. 4-222527, U.S. Pat. No. 5,591,616, EP-A-0 604 662). Its structure is shown in FIG. 1. This plasmid comprises a plasmid called pTOK154 which can replicate in both *Escherichia coli* and in *Agrobacterium tumefaciens* (pTOK154 is a plasmid containing T region, which was constructed by the method described below from a known plasmid pGA472 derived from the Ti plasmid and a known plasmid having a wide host spectrum called pVCK101), into which a KpnI fragment (containing virB, virG and virc genes) with a size of 15.2 kb originated from the virulence region of pTiBo542 has been inserted, the KpnI fragment having been cloned. In pTOK154, between two border sequences of the T region, a kanamycin-resistant gene is inserted as a gene to be introduced into Indica rice. This is an embodiment wherein the gene desired to be introduced into Indica rice is arranged in a plasmid having the cloned DNA fragment originated from the virulence region of pTiBo542. A vector pTOK233 (Hiei et al., supra) is also a preferred example of a super binary vector, which was derived from pTOK162 and pGL2-IG (WO95/06722), which has a hygromycin-resistant gene (hpt) and an intron GUS gene of castor-oil plant inserted in the T-DNA region of pTOK162 by homologous recombination. The structure of pTOK233 is also shown in FIG. 1.

The gene which is desired to be incorporated into Indica rice may be inserted into a restriction site in the T-DNA region of the above-described plasmid, and the desired recombinant plasmid may be selected depending on an appropriate selective marker such as drug resistance and the like which the plasmid has. However, if the vector, such as pTOK162 shown in FIG. 1, is large and has a number of restriction sites, it is not always easy to insert the desired DNA into the T region of the vector by conventional sub-cloning methods. In such a case, the desired DNA can be inserted into pTOK162 by utilizing the in vivo homologous recombination (Herrera-Esterella L. et al., 1983; EMBO J. 2:987–995, Horsch R. H. et al., 1984; Science 223:496–498) in the cells of *Agrobacterium tumefaciens*. That is, for example, pTOK162 is first introduced into *Agrobacterium tumefaciens* and the plasmid pBR322 (or a similar plasmid) containing the desired DNA is further introduced thereinto. Since the DNA of pTOK162 has a region homologous with that of pBR322, the pBR322 derivative containing the desired gene is to be inserted into pTOK162 by the genetic recombination via the homologous regions. Unlike pTOK162, pBR322 cannot replicate by itself in *Agrobacterium tumefaciens*. Therefore, pBR322 can only be alive in *Agrobacterium tumefaciens* in the inserted form in pTOK162 (the recombined pTOK162 and pBR322 is hereinafter referred to as "pTOK162::pBR322 derivative"). By selecting the transformants based on the selective marker (such as drug resistance) specific to each of pTOK162 and pBR322 derivative, *Agrobacterium tumefaciens* transformants containing pTOK162::pBR322 derivative may be obtained. The present inventors made a study by introducing various plasmids into *Agrobacterium tumefaciens* containing pTOK162 to discover that, as the selection marker of the pBR322 derivative, spectinomycin-resistant gene (SP) originated from transposon Tn7 (De Greve, H. H. et al., 1981; Plasmid 6:235–248) is excellent. Thus, in cases where the desired gene has already been cloned into pBR322, by inserting SP gene into the plasmid, the desired gene can be inserted into the T region of pTOK162 by homologous recombination in vivo in *Agrobacterium tumefaciens*. Alternatively, a plasmid containing a DNA originated from pBR322 and SP gene is first provided, and the desired gene may be inserted into this plasmid. In this case, by utilizing the border sequences of the T region, it is possible to finally arrange the kanamycin-resistant gene and the desired gene in separate T regions in pTOK162. When plants are transformed using the resistance to kanamycin as a marker, there is a substantial probability that both T regions are introduced, and the introduction of the desired gene can be sufficiently attained. Further, in this case, since both T regions may be inserted into different chromosomes, it may be possible to subsequently segregate the desired gene from the kanamycin-resistant gene.

As the host bacteria belonging to genus Agrobacterium, *Agrobacterium tumefaciens* may preferably be employed, although not restricted.

The introduction of a plasmid into the bacteria belonging to the genus Agrobacterium such as *Agrobacterium tumefaciens* can be carried out by a conventional method such as triparental mating method of bacteria (Ditta G. et al., 1980; Proc. Natl. Acad. Sci. USA, 77:7347–7351).

Since the Agrobacterium prepared as mentioned above has highly efficient virulence genes originated from pTOK162, transformation of Indica rice can be attained with a high efficiency.

It should be noted that in the method of the present invention, the gene which is desired to be introduced into Indica rice is arranged between border sequences of the T region as in the prior art, and the desired gene may be arranged in the Ti plasmid or in another plasmid in the Agrobacterium.

The transformation of the immature embryos of Indica rice by the Agrobacterium may be carried out by merely contacting the immature embryos with the Agrobacterium. For example, a cell suspension of the Agrobacterium having a population density of approximately from $10^6$ to $10^{11}$ cells/ml is prepared and the immature embryos are immersed in this suspension for about 3 to 10 minutes. The resulting immature embryos are then cultured on a solid medium for several days together with the Agrobacterium. The immature embryos need not be subjected to a dedifferentiation treatment such as culturing in the presence of 2,4-D.

It is preferred that the thus transformed immature embryos be selected and grown under dedifferentiated condition. The selection may be effected on the basis of the expression of the above-mentioned desired gene and a marker (drug resistance and the like). The dedifferentiated cells are desired to be in the form of a callus having an ability to produce normal plants.

In the method of the present invention, the selection of the transformed cells is carried out on the medium having the above-described composition and pH. In the above-described composition, a preferred example of the cytokinin is 6-benzylaminopurine. In the above-described composition, preferred examples of the sugar include maltose, sucrose and glucose as well as mixtures thereof. Examples of the gelling agent include agar, agarose, gelan-gum and the like. Such a gelling agent is for gelling the medium and the content thereof is not restricted as long as gelling of the medium is attained. Usually, the amount of the gelling agent is about 2 to 10 g/l. The medium further comprising at least 0.5 to 2 mg/l of KI, 0.7 to 5 mg/l of $ZnSO_4$, 0.1 to 0.3 mg/l of $Na_2MoO_4$, 0.01 to 0.02 mg/l of $CuSO_4$, 0.01 to 0.02 mg/l of $CoCl_2$, 0.25 to 10 mg/l of nicotinic acid, 0.25 to 5 mg/l of pyridoxine, and 0.05 to 20 mg/l of thiamin in addition to the above-described composition may also preferably be used. The medium still further comprising at least 100 to 3000 mg/l of Casamino acid, 100 to 3000 mg/l of proline, 100 to 3000 mg/l of glutamine and 0.01 to 5 mg/l of α-naphthaleneacetic acid in addition to the composition just mentioned above may also preferably be used. The medium further comprising 1000 to 60,000 mg/l of a sugar alcohol in addition to each of the above-described compositions may also preferably be used. Preferred examples of the sugar alcohol include mannitol, sorbitol and the like. In cases where selection is carried out based on a drug resistance, the medium contains, needless to say, the drug in addition to the above-mentioned compositions. It is preferred to carry out the selection 2 to 5 times. In this case, the duration of the first selection may preferably be about 2 to 3 weeks and the duration of the second selection may preferably be about 2 weeks. In cases where selection is made at a plurality of times, all of the selections are carried out on the medium described above. However, different selection steps may be carried out on different media having different contents of the components but within the ranges mentioned above.

The regeneration of plants from the transformed cells may be effected by known methods (Rance et al., 1994 (supra)). In this case, it is preferred to add the drug for selection also to the regeneration medium. In this way, plants which acquired the desired character by the transformation, preferably transformed plants which acquired the desired character and have normal fertility can be regenerated. These steps are concretely illustrated in the following examples.

The present invention will now be described more concretely by way of examples thereof. It should be noted, however, the following examples are presented for the illustration purpose only and should not be interpreted in any restrictive way.

Example 1, Comparative Examples 1–3

(1) Agrobacterium strain and Plasmid

As the host bacterium, LBA4404 (ATCC 37349) was used and the above-described pTOK233 (see FIG. 1) was used as a vector.

(2) Sample Varieties and Tissues

As the sample varieties, IR8, IR24, IR26, IR36, IR54, IR64, IR72, Xin Qing Ai 1, Nan Jin 11 and Suewon 258 were used. Immature seeds on 10 to 14 days after flowering were husked and sterilized in 70% ethanol for several seconds and then in aqueous 1% sodium hypochlorite solution containing Tween 20 for 15 minutes. After washing the seeds several times with sterilized water, immature embryos with lengths of 1.5 to 2 mm were excised under a stereoscopic microscope.

(3) Inoculation and Cocultivation

Colonies of Agrobacterium cultured on AB medium (Chilton M-D. et al. (1974) *Agrobacterium tumefaciens* DNA and PS8 bacteriophage DNA not detected in crown gall tumors. Proc. Natl. Acad. Sci. USA, 71:3672–3676) containing 50 mg/l of hygromycin and 50 mg/l of kanamycin for 3 to 7 days were recovered with a platinum loop and suspended in AAM medium (Hiei et al., 1994, supra) to prepare an inoculation solution. The population density of the bacterial cells was adjusted to $2\times10^8$ to $3\times10^8$ cells/ml.

To the excised immature embryos, 1 ml of the bacterial cell suspension was added and the resulting mixture was agitated with a vortex mixer for about 30 seconds. After leaving the resultant to stand for 5 to 10 minutes, the immature embryos to which the bacterial cell suspension was attached was placed on NB-AS medium for cocultivation such that the scutella face upside, and cocultivation was carried out in the dark at 25° C. for 4 to 5 days. The composition of the NB-AS medium used here was the same as the NB medium described in Rance et al. (1994) (supra) except that the former did not contain L-glutamine, and further contained 100 $\mu$M of acetosyringone, 20 g/l of sucrose, 10 g/l of D-glucose and 12.5 g/l of Sea Plaque agarose. That is, the composition of the medium was as follows: $KNO_3$ 2830 mg/l, $MgSO_4.7H_2O$ 185 mg/l, $KH_2PO_4$ 400 mg/l, $CaCl_2.2H_2O$ 166 mg/l, $(NH_4)_2.SO_4$ 463 mg/l, KI 0.7 mg/l, $H_3BO_3$ 3.0 mg/l $MnSO_4.H_2O$ 10 mg/l, $ZnSO_4.7H_2O$ 2.0 mg/l, $Na_2MoO_4.2H_2O$ 0.25 mg/l, $CuSO_4.5H_2O$ 0.025 mg/l, $CoCl_2.6H_2O$ 0.025 mg/l, $Na_2.EDTA$ 37.3 mg/l, $Fe_2SO_4.7H_2O$ 27.8 mg/l, myoinositol 100 mg/l, nicotinic acid 1.0 mg/l, pyridoxine hydrochloride 1.0 mg/l, thiamin hydrochloride 10 mg/l, Casamino acid 300 mg/l, L-proline 300 mg/l, 2, 4-dichlorophenoxyacetic acid 2 mg/l, $\alpha$-naphthaleneacetic acid 1 mg/l, 6-benzylaminopurine 1 mg/l, acetosyringone 100 $\mu$M, sucrose 20 g/l, D-glucose 10 g/l, Sea Plaque agarose 12.5 g/l, pH 5.2.

(4) Selection of Transformed Cells

After the cocultivation, the elongated shoots were removed with a scalpel and the immature embryos were transplanted to NBM medium containing 3 mg/l of hygromycin, followed by culturing the immature embryos in the dark at 30° C. for 3 to 4 days. The immature embryos were then transplanted to each of the first selection media which were NBM medium (Example 1), 2N6M medium (Comparative Example 1), CCM medium (Comparative Example 2) and MSM (Comparative Example 3), each of which contained 20 to 50 mg/l of hygromycin, and cultured under illumination at 30° C. for 2 to 3 weeks. The hygromycin-resistant calli formed on the scutella of the immature embryos were transplanted to NB2 medium containing 20 mg/l of hygromycin or to CCM medium containing 30 mg/l of hygromycin, and the second selection was carried out under illumination at 30° C. for 2 weeks. Compact and embryogenic calli were selected and grown on the above-mentioned NB2 medium or on CCM medium containing 50 mg/l of hygromycin for 1 to 3 times (3–5th selection) at 10 to 14 days' intervals. The compositions of the NBM, 2N6M, CCM, MSM and NB2 media used here are shown below. The used selection media contained 250 mg/l of cefotaxime in addition to the compositions described below.

NBM Medium $KNO_3$ 2830 mg/l, $MgSO_4.7H_2O$ 185 mg/l, $KH_2PO_4$ 400 mg/l, $CaCl_2.2H_2O$ 166 mg/l, $(NH_4)_2.SO_4$ 463 mg/l, KI 0.75 mg/l, $H_3BO_3$ 3.0 mg/l, $MnSO_4.H_2O$ 10 mg/l, $ZnSO_4.7H_2O$ 2.0 mg/l, $Na_2MoO_4.2H_2O$ 0.25 mg/l, $CuSO_4.5H_2O$ 0.025 mg/l, $CoCl_2.6H_2O$ 0.025 mg/l, $Na_2.EDTA$ 37.3 mg/l, $Fe_2SO_4.7H_2O$ 27.8 mg/l, myoinositol 100 mg/l, nicotinic acid 1.0 mg/l, pyridoxine hydrochloride 1.0 mg/l, thiamin hydrochloride 10 mg/l, Casamino acid 300 mg/l, L-proline 300 mg/l, L-glutamine 300 mg/l, 2,4-dichlorophenoxyacetic acid 2 mg/l, $\alpha$-naphthaleneacetic acid 1 mg/l, 6-benzylaminopurine 1 mg/l, D-maltose 30 g/l, gelangum (trademark GELRITE, commercially available from Sigma) 2.5 g/l, pH 5.8.

2N6M Medium

N6 inorganic salts, N6 vitamins (Chu C. -C. (1978) The N6 medium and its applications to anther culture of cereal crops. In proc. Symp. Plant Tissue Culture. Peking: Science Press, pp. 43–50) to which 1 g/l of Casamino acid, 2 mg/l of 2,4-dichlorophenoxyacetic acid, 30 g/l of D-maltose and 2.5 g/l of gelangum (trademark GELRITE, commercially available from Sigma) were added. That is, the medium had the following composition: $KNO_3$ 2830 mg/l, $MgSO_4.7H_2O$ 185 mg/l, $KH_2PO_4$ 400 mg/l, $CaCl_2.2H_2O$ 166 mg/l, $(NH_4)_2.SO_4$ 463 mg/l, KI 0.8 mg/l, $H_3BO_3$ 1.6 mg/l, $MnSO_4.4H_2O$ 3.3 mg/l, $ZnSO_4.7H_2O$ 1.5 mg/l, $Na_2MoO_4.2H_2O$ 0.25 mg/l, $CuSO_4$ $5H_2O$ 0.025 mg/l, $Na_2.EDTA$ 37.3 mg/l, $Fe_2SO_4.7H_2O$ 27.8 mg/l, nicotinic acid 0.5 mg/l, pyridoxine hydrochloride 0.5 mg/l, thiamin hydrochloride 1.0 mg/l, Casamino acid 1 g/l, glycine 2 mg/l, 2,4-dichlorophenoxyacetic acid 2 mg/l, D-maltose 30 g/l, gelangum (trademark GELRITE, commercially available from Sigma) 2.5 g/l, pH 5.8.

CCM Medium

CC medium (Potrykus I et al(1979) Callus formation from cell culture protoplasts of corn (Zea mays L.). Theor. Appl. Genet. 54:209–214; Hartke S. et al (1989) Somatic embryogenesis and plant regeneration from various Indica rice (*Oryza Sativa L.*) genotypes. J. Genet & Breed. 43: 205–214) to which 30 g/l of D-maltose, 2 mg/l of 2,4-dichlorophenoxyacetic acid and 2.5 g/l of gelangum (trademark GELRITE, commercially available from Sigma) were added. That is, the medium had the following composition: $KNO_3$ 1212 mg/l, $NH_4NO_3$ 640 mg/l, $CaCl_2.2H_2O$ 588 mg/l, $MgSO_4.7H_2O$ 247 mg/l, $KH_2PO_4$ 136 mg/l, $FeSO_4.7H_2O$ 27.8 mg/l, $Na_2EDTA$ 37.3 mg/l, $H_3BO_3$ 3.1 mg/l, $MnSO_4.4H_2O$ 11.15 mg/l, $ZnSO_4.7H_2O$ 5.76 mg/l, KI 0.83 mg/l, $Na_2MoO_4$ $2H_2O$ 0.24 mg/l, $CuSO_4.5H_2O$ 0.025 mg/l, $CoSO_4.7H_2O$ 0.028 mg/l, nicotinic acid 6 mg/l, thiamin hydrochloride 8.5 mg/l, pyridoxine hydrochloride 1 mg/l, glycine 2 mg/l, myoinositol 90 mg/l, coconut water 100 ml/l(commercially available from Gibco), mannitol 36.43 g/l, D-maltose 30 g/l, 2,4-dichlorophenoxyacetic acid 2 mg/l, gelangum (trademark GELRITE, commercially available from Sigma) 2.5 g/l, pH 5.8.

MSM Medium

MS inorganic salts, MS vitamins (Murashige, T. and Skoog, F. (1962) A revised medium for rapid growth and bioassays with tobacco tissue cultures. Physiol. Plant. 15: 473–497) to which 1 g/l of Casamino acid, 30 g/l of D-maltose, 2 mg/l of 2,4-dichlorophenoxyacetic acid and 2.5 g/l of gelangum (trademark GELRITE, commercially available from Sigma) were added. That is, the medium had the following composition: $NH_4NO_3$ 1650 mg/l, $KNO_3$ 1900 mg/l, $MgSO_4.7H_2O$ 370 mg/l, $KH_2PO_4$ 170 mg/l, $CaCl_2.2H_2O$ 440 mg/l, KI 0.83 mg/l, $H_3BO_3$ 6.2 mg/l, $MnSO_4.4H_2O$ 22.3 mg/l, $ZnSO_4.7H_2O$ 8.6 mg/l, $Na_2MoO_4.2H_2O$ 0.25 mg/l, $CuSO_4.5H_2O$ 0.025 mg/l, $CoCl_2$ $0.6H_2O$ 0.025 mg/l, $Na_2.EDTA$ 37.3 mg/l, $Fe_2SO_4.7H_2O$ 27.8 mg/l, myoinositol 100 mg/l, nicotinic acid 0.5 mg/l, pyridoxine hydrochloride 0.5 mg/l, thiamin hydrochloride 0.1 mg/l, glycine 2.0 mg/l, Casamino acid 1 g/l, 2,4-dichlorophenoxyacetic acid 2 mg/l, D-maltose 30 g/l, gelangum (trademark GELRITE, commercially available from Sigma) 2.5 g/l, pH 5.8.

NB2 Medium $KNO_3$ 2830 mg/l, $MgSO_4.7H_2O$ 185 mg/l, $KH_2PO_4$ 400 mg/l, $CaCl_2.2H_2O$ 166 mg/l, $(NH_4)_2.SO_4$ 463 mg/l, KI 0.7 mg/l, $H_3BO_3$ 3.0 mg/l, $MnSO_4.H_2O$ 10 mg/l, $ZnSO_4.7H_2O$ 2.0 mg/l, $Na_2MoO_4.2H_2O$ 0.25 mg/l, $CuSO_4.5H_2O$ 0.025 mg/l, $CoCl_2.6H_2O$ 0.025 mg/l, $Na_2.EDTA$ 37.3 mg/l, $Fe_2SO_4.7H_2O$ 27.8 mg/l, myoinositol 100 mg/l, nicotinic acid 1.0 mg/l, pyridoxine hydrochloride 1.0 mg/l, thiamin hydrochloride 10 mg/l, Casamino acid 300 mg/l, L-proline 300 mg/l, L-glutamine 300 mg/l, 2,4-dichlorophenoxyacetic acid 2 mg/l, α-naphthaleneacetic acid 1 mg/l, 6-benzylaminopurine 0.2 mg/l, D-maltose 30 g/l, D-mannitol 30 g/l, gelangum (trademark GELRITE, commercially available from Sigma) 2.5 g/l, pH 5.8.

The selected calli were transplanted to NBM regeneration preculture medium containing 40 mg/l of hygromycin and cultured under illumination at 30° C. for about 10 days.

(5) Checking of Regeneration of Transformants and Expression of GUS

The hygromycin-resistant embryogenic calli obtained by the preculture of regeneration were dried in a petri dish in which a filter paper was laid (Rance et al., 1994 (supra)), and the calli were placed on RNM regeneration medium (containing 30 mg/l of hygromycin) which had the same composition as the RN medium (Rance et al., 1994, (supra)) except that the sugar source was replaced with 30 g/l of D-maltose. Two to three weeks after, the regenerated plants were transplanted to MSI rooting medium (half concentrations of MS major inorganic salts, MS minor inorganic salts and MS vitamins, 1 g/l of Casamino acid, 0.2 mg/l of indolebutyric acid, 15 g/l of sucrose and 3 g/l of GELRITE, pH 5.8) and cultivated under illumination at 25° C. for about 3 weeks. Pieces of leaves of the obtained hygromycin-resistant regenerated plants were subjected to X-Gluc treatment so as to check GUS expression (Hiei et al., 1994, supra). The regenerated plants were then transplanted to 500-fold diluted aqueous Hyponex solution and grown under illumination at 25° C. for 10 days, followed by transplanting the plants to pots in a greenhouse.

(6) Southern Analysis of Transformants and Expression of Introduced Gene in Subsequent Generations The DNAs extracted from leaves of the regenerated plants which expressed GUS were digested by restriction enzyme Hind III or Kpn I and Southern analysis using hpt or GUS gene as a probe was carried out. The Southern analysis was carried out by the method described by Sambrook et al. (1990) (Sambrook, J. et al.,Molecular cloning: A Laboratory Manual, 2nd Edn. Cold Spring Harbor, N.Y.: Cold Spring Harbor Laboratory Press). The transformants were self-pollinated and the seeds of the next generation was sown on hormone-free MS medium. After germination, GUS expression was checked by X-Gluc treatment of pieces of leaves. The seedlings were transplanted to hormone-free MS medium containing 50 mg/l of hygromycin and resistance to hygromycin was checked.

The results are shown in Tables 1 and 2.

TABLE 1

Comparison of Basal Media in First Selection (Variety: IR24, Strain: LBA4404/pTOK233)

| Medium for 1st Selection | Concentration of Hygromycin (mg/l) | Number of Sample Immature Embryos (A) | Number of Calli Selected 1st | 3rd | Preculture | Number of Redifferentiated Lines | Number of GUS+ Regenerated Lines (B)* | Transformation Efficiency (B/A: %) |
|---|---|---|---|---|---|---|---|---|
| 2N6M | 20 | 26 | 18 | 3 | 3 | 2 | 2 | 7.7 |
| MSM | 50 | 28 | 15 | 2 | 1 | 0 | 0 | 0.0 |
| CCM | 50 | 25 | 12 | 6 | 2 | 1 | 1 | 4.0 |
| NBM | 20 | 32 | 60 | 18 | 13 | 11 | 11 | 34.4 |
| NBM | 20 | 120 | 240 | 123 | 76 | 67 | 63 | 52.5 |

*Number of independent GUS+ plant lines (Clones are not included.)
NB2 medium (20 mg/l of hygromycin) was used for the second and third selections.
NBM medium (40 mg/l of hygromycin) was used for the preculture of regeneration.
RNM medium (30 mg/l of hygromycin) was used for regeneration.

TABLE 2

Comparison of Basal Media in First Selection (Variety: IR36, Strain: LBA4404/pTOK233)

| Medium for 1st Selection | Concentration of Hygromycin (mg/l) | Number of Sample Immature Embryos (A) | Number of Calli Selected 1st | 3rd | Preculture | Number of Redifferentiated Lines | Number of GUS+ Regenerated Lines (B)* | Transformation Efficiency (B/A: %) |
|---|---|---|---|---|---|---|---|---|
| 2N6M | 20 | 35 | 18 | 6 | 6 | 2 | 2 | 5.7 |
| CCM | 50 | 32 | 12 | 8 | 8 | 4 | 3 | 9.4 |
| NBM | 20 | 35 | 53 | 33 | 20 | 15 | 14 | 40.0 |
| NBM | 20 | 90 | 162 | 85 | 37 | 34 | 33 | 36.7 |
| NBM | 20 | 100 | 185 | 112 | 59 | 52 | 50 | 50.0 |

*Number of independent GUS+ plant lines (Clones are not included.)
CCM medium (30 mg/l of hygromycin) was used for the second selection.
CCM medium (50 mg/l of hygromycin) was used for the third to fifth selections.
NB medium (40 mg/l of hygromycin) was used for the preculture of regeneration.
RNM medium (30 mg/l of hygromycin) was used for regeneration.

TABLE 3

Results of Transformation of Indica Rice by LBA4404/pTOK233

| Variety | Number of Sample Immature Embryos (A) | Number of Selected HygR Calli Lines | Number of Redifferentiated Lines | Number of GUS+ Regenerated Lines (B)* | Transformation Efficiency (B/A: %) |
|---|---|---|---|---|---|
| IR8 | 60 | 31 | 19 | 18 | 30.0 |
| IR24 | 32 | 13 | 11 | 11 | 34.4 |
|  | 120 | 76 | 67 | 63 | 52.5 |
| IR26 | 63 | 38 | 28 | 27 | 42.9 |
| IR36** | 35 | 20 | 15 | 14 | 40.0 |
|  | 90 | 37 | 34 | 33 | 36.7 |
|  | 100 | 59 | 52 | 50 | 50.0 |
| IR54 | 42 | 23 | 20 | 19 | 45.2 |
|  | 30 | 38 | 13 | 13 | 43.3 |
| IR64 | 79 | 76 | 53 | 50 | 63.3 |
| IR72** | 50 | 30 | 28 | 28 | 56.0 |
| Nan Jin 11 | 57 | 31 | 23 | 21 | 36.8 |
| Suewon 258 | 57 | 35 | 25 | 24 | 42.1 |
| Xin Qing Ai 1 | 40 | 27 | 19 | 18 | 45.0 |

*Number of independent GUS+ plant lines (Clones are not included.)
**CCM medium was used for the second and the subsequent selections.

The results of the above-described experiments will now be further explained.

(1) Selection of Transformed Cells After the culturing for 2 to 3 weeks on the first selection medium, hygromycin-resistant calli were obtained at a much higher frequency when the medium was NBM medium than in the cases where CCM, MSM or 2N6M medium was used. The immature embryos during the first selection step were checked for the expression of the GUS gene by X-Gluc treatment. As a result, it was confirmed that a plurality of cell clumps formed on the scutella of the immature embryos cultured on the NBM medium uniformly expressed GUS. As for those cultured on the CCM medium or MSM medium, the entire scutella swelled and specific growth of the GUS-expressing region was not substantially observed. That is, when the NBM medium was used, since the regions into which the gene was introduced exhibited selective growth, a plurality of independent hygromycin-resistant cell clumps were obtained per one immature embryo. On the other hand, when the CCM medium or MSM medium was used, selective growth of the gene-introduced regions was not observed and the entire surface cells of the scutella tended to form calli. Therefore, when the first selection was carried out on the CCM or MSM medium, it was difficult to identify and select the hygromycin-resistant cell agglomerates.

In cases where the concentration of hygromycin in the CCM or MSM medium was as low as 20 mg/l or 30 mg/l, the entire scutella grew as in the cases where hygromycin was not added. When the 2N6M medium was used, the number of calli selected from the immature embryos was small and the growth tended to be slow. Christou et al. used MS and CC media for selection of transformed cells in the particle gun method (Christou P. et al.,(1991) Production of transgenic rice (Oryza Sativa L.) plants from agronomically important Indica and japonica varieties via electric discharge particle acceleration of exogenous DNA into immature zygotic embryos. Bio/technology 9: 957–962; Christou P., Ford, T. L. and Kofron, M. (1992) The development of a variety-independent gene-transfer method for rice. TIB TECH 10: 239–246). However, as in the Comparative Examples of the present invention, the number of obtained transformants was small.

It was difficult to obtain embryogenic resistant calli which had redifferentiation ability when the NBM medium from which NAA and BA were removed and so which contained 2,4-D alone. From this, it is thought that a cytokinin such as BA is necessary to induce an embryogenic callus having regeneration ability. Li et al. (1993) (supra) reported that they selected transformed cells on the NB medium which did not contain NAA, BA and L-glutamine and obtained only a small number of regenerated plants of Indica rice, which results are coincident with the results of the Comparative Examples of the present invention.

The culturing duration for the first selection is preferably 2 to 3 weeks. If culture is continued for a period longer than this, the calli formed on the scutella of the immature embryos unnecessarily grow, so that it is difficult to select a plurality of independent calli per one immature embryo and the morphology of the calli tended to be bad.

(2) Culturing for Second and Later Selection

With 8 varieties among the 10 varieties tested, embryogenic calli grew on the NB2 medium. As for the 2 varieties IR36 and IR72, calli with better morphology were able to be kept on the CCM medium (30 to 50 mg/l of hygromycin, 250 mg/l of cefotaxime) than on the NB2 medium.

In the test group for which the first selection was carried out on the NBM medium, much more calli retained resistance in the second and third selections than in the groups for which other media were used (Tables 1 and 2). The culturings for the second and the subsequent selections were carried out for about every 2 weeks. If the culturing is continued for 3 weeks or more, the calli tended to brown and the morphology thereof tended to be bad. Preculture for regeneration was carried out after third, fourth or fifth selection.

(3) Redifferentiation Culturing

Redifferentiated plants were efficiently obtained for all of the 10 varieties and no varieties were difficult to regenerate. As the rooting medium, the MSI medium to which IBA (0.2 mg/l) was added was better than the hormone-free medium because it clearly accelerated rooting. Addition of hygromycin (30 mg/l) to the rooting medium was effective for the selection of hygromycin-resistant plants at the stage of plant.

(4) Transformation Efficiency

The leaves of most of the regenerated plants exhibited uniform GUS expression (Table 3). When the first selection was carried out on the NBM medium, transformants which were hygromycin-resistant and which exhibited GUS expression were obtained at frequencies as high as not less than 30% per immature embryo for all of the tested 10 varieties (Tables 1, 2 and 3).

(5) Southern Analysis and Inheritance to Subsequent Generations

Southern analysis confirmed existence of the introduced gene in all of the tested regenerated plants which exhibited GUS expression and the T-DNA in each plant was inserted into a random location which was different from plant to plant. Further, GUS expression and resistance to hygromycin were checked for the subsequent generations. As a result, genetic segregation in accordance with Mendel's law was observed.

What is claimed is:

1. A method for transforming rice comprising transforming immature embryo cells of Indica rice by *Agrobacterium tumefaciens* and selecting transformed cells by using a drug for selection, characterized in that a medium containing 2000 to 4000 mg/l of $KNO_3$, 60 to 200 mg/l of $MgSO_4$, 200 to 600 mg/l of $KH_2PO_4$, 100 to 450 mg/l of $CaCl_2$, 200 to 600 mg/l of $(NH_4)_2.SO_4$, 1 to 7 mg/l of $H_3BO_3$, 2 to 20 mg/l of $MnSO_4$, 20 to 50 mg/l of EDTA or a salt thereof, 3 to 8 mg/l of Fe, 50 to 200 mg/l of myoinositol, 0.5 to 10 mg/l of 2,4-dichlorophenoxyacetic acid, 0.01 to 5 mg/l of a cytokinin, 5000 to 80,000 mg/l of a sugar, and a gelling agent, which medium has a pH of 4.5 to 6.5, is used as a medium for selecting said transformed cells.

2. The method according to claim 1, wherein said cytokinin is 6-benzylaminopurine.

3. The method according to claim 1, wherein said sugar is at least one selected from the group consisting of maltose, sucrose and glucose.

4. The method according to claim 1, wherein said medium further comprises at least 0.5 to 2 mg/l of KI, 0.7 to 5 mg/l of $ZnSO_4$, 0.1 to 0.3 mg/l of $Na_2MoO_4$, 0.01 to 0.02 mg/l of $CuSO_4$, 0.01 to 0.02 mg/l of $CoCl_2$, 0.25 to 10 mg/l of nicotinic acid, 0.25 to 5 mg/l of pyridoxine, and 0.05 to 20 mg/l of thiamin.

5. The method according to claim 4, wherein said medium further comprises at least 100 to 3000 mg/l of Casamino acid, 100 to 3000 mg/l of proline, 100 to 3000 mg/l of glutamine and 0.01 to 5 mg/l of α-naphthaleneacetic acid.

6. The method according to claim 1, wherein said medium further comprises 1000 to 60,000 mg/l of a sugar alcohol.

7. The method according to claim 6, wherein said sugar alcohol is mannitol or sorbitol.

8. The method according to claim 1, wherein said Indica rice belongs to Group I.

9. The method according to claim 1, wherein the gelling agent is agar, agarose or gelangum.

10. The method according to claim 1 wherein a gene to be introduced into the embryo cells is inserted into the Ti plasmid of the *Agrobacterium tumefaciens*.

* * * * *